United States Patent [19]

Fuss et al.

[11] Patent Number: 4,574,912
[45] Date of Patent: Mar. 11, 1986

[54] EAR MUFF HEARING AID

[76] Inventors: Gary E. Fuss; George Spector, both of 233 Broadway Rm 3615, both of New York, N.Y. 10007

[21] Appl. No.: 671,207

[22] Filed: Nov. 14, 1984

[51] Int. Cl.⁴ .................................................. H04R 25/00
[52] U.S. Cl. ..................................... 181/129; 181/136
[58] Field of Search ........................ 181/129, 133, 136

[56] References Cited

U.S. PATENT DOCUMENTS

| | | | |
|---|---|---|---|
| 1,366,193 | 1/1921 | Lalieff | 181/136 |
| 1,757,966 | 5/1930 | Kaplick | 181/136 |
| 3,938,616 | 2/1976 | Brownfield | 181/136 |
| 4,457,396 | 7/1984 | James | 181/136 |

Primary Examiner—Benjamin R. Fuller

[57] ABSTRACT

An acoustic device for amplifying sound is provided and consists of a pair of ear extenders secured to a head band so that the head band may be positioned on a listener's head with the ear extenders transversely in contact with the listener's head behind the ears whereby sounds are amplified and transmitted into the ears.

6 Claims, 7 Drawing Figures

U.S. Patent  Mar. 11, 1986  4,574,912
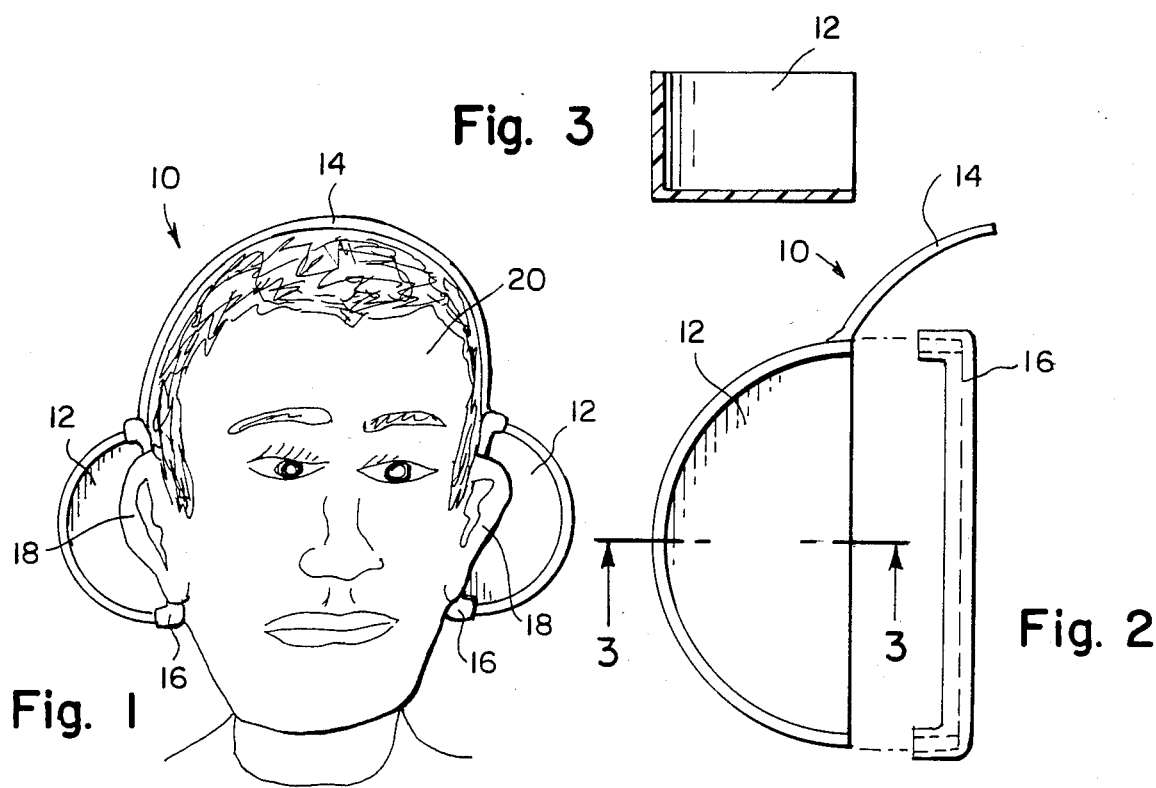
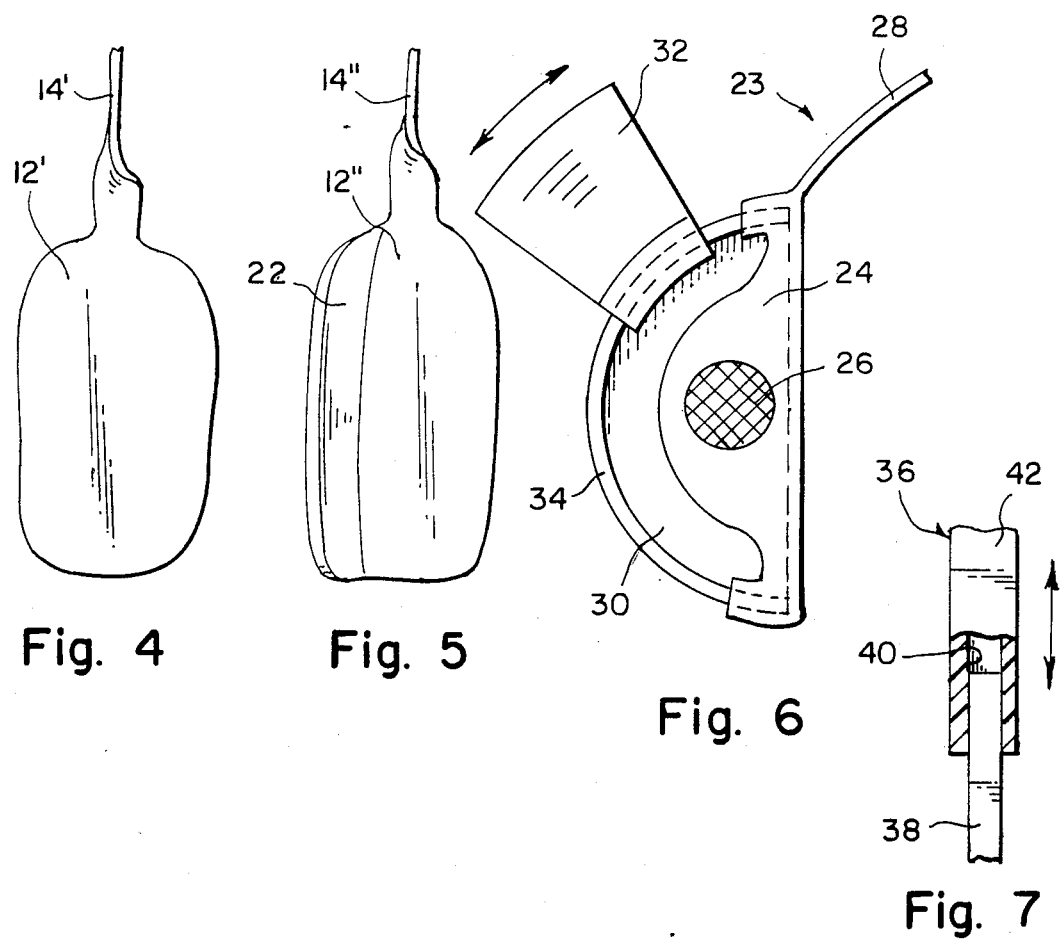

EAR MUFF HEARING AID

BACKGROUND OF THE INVENTION

The instant invention relates generally to sound amplification apparatuses and more specifically it relates to an acoustic device for amplifying sounds such as coming from a T.V. set or the like.

Numerous sound amplification apparatuses have been provided in prior art that are adapted to mechanically carry sounds to the human ear. For example U.S. Pat. Nos. 824,773; 1,453,969 and 3,513,937 all are illustrative of such prior art. While these units may be suitable for the particular purpose to which they address, they would not be as suitable for the purposes of the present invention as heretofore described.

SUMMARY OF THE INVENTION

A principle object of the present invention is to provide an acoustic device for amplifying sounds that utilizes a pair of ear extenders secured to a head band that is positioned on a listener's head with the ear extenders transversely in contact with the listener's head behind the ears whereby sounds are amplified and transmitted into the ears.

Another object is to provide an acoustic device for amplifying sounds that is lightweight and has pads on the ear extenders for a comfortable fit on the listener's head.

An additional object is to provide an acoustic device for amplifying sounds that has earphones mounted within the pads attached directly to the head band with snap on cup shaped ear extenders having adjustable flared members attached thereto so that when the cup shaped ear extenders are removed from the pads the earphones can be used independently from the ear extenders.

A further object is to provide an acoustic device for amplifying sounds that is simple and easy to use.

A still further object is to provide an acoustic device for amplifying sounds that is economical in cost to manufacture.

Further objects of the invention will appear as the description proceeds.

To the accomplishment of the above and related objects, this invention may be embodied in the form illustrated in the accompanying drawings, attention being called to the fact, however, that the drawings are illustrative only, and that changes may be made in the specific construction illustrated and described within the scope of the appended claims.

BRIEF DESCRIPTION OF THE DRAWING FIGURES

FIG. 1 is an elevational view of the invention in use mounted on the listener's head.

FIG. 2 is an enlarged elevational view of a portion of the invention showing one of the cup shaped ear extenders with pad exploded therefrom.

FIG. 3 is a cross sectional view taken along line 3—3 in FIG. 2.

FIG. 4 is an enlarged elevational view of a flat shaped ear extender.

FIG. 5 is an enlarged elevational view of a flat shaped ear extender bent along one side.

FIG. 6 is an enlarged elevational view of a modified snap in cup shaped ear extender showing an adjustable flared member attached thereto and an earphone mounted within a pad that can be used independently from the ear extender.

FIG. 7 is a partial top view of the head band with parts broken away showing an adjustable feature.

DETAILED DESCRIPTION OF THE PREFERRED EMBODIMENTS

Turning now descriptively to the drawings, in which similar reference characters denote similar elements throughout the several views, FIGS. 1 through 3 illustrates an acoustic device 10 for amplifying sounds such as from a T.V. set or the like. The device 10 consists of a pair of ear extenders 12, a head band 14 and a pair of relatively soft pads 16.

Each ear extender 12 is cup shaped, larger than a normal adult human ear 18 and is constructed out of lightweight sound reflective material such as plastic. The head band 14 is adapted to fit about a listener's head 20. The ear extenders 12 are secured to the head band 14 so that the head band may be positioned on the listener's head 20 with the ear extenders transversely in contact with the listener's head behind the ears 18 whereby sounds are amplified and transmitted into the ears. Each pad 16 is mounted to each of the ear extenders 12 so as to make contact with the listener's head 20 behind the ears 18 for a comfortable fit thereon.

FIG. 4 shows another type of ear extender 12' wherein the ear extender is flat shaped and the head band 14' is twisted so that the ear extender 12' is in proper position with respect to the ear 18.

FIG. 5 shows still another type of ear extender 12" wherein the ear extender is flat shaped and is bent along one side as indicated by numeral 22. The head band 14" is also twisted so that the ear extenders 12" is in proper position with respect to the ear 18.

FIG. 6 shows one side of a modified acoustic device 23 which contains a pair of relatively soft pads 24, a pair of ear phones 26, a head band 28 and a pair of snap on cup shaped ear extenders 30.

Each earphone 26 is mounted within one of the pads 24. The head band 28 is adapted to fit about the listener's head 20 and the pads 24 are secured to the head band 28. The head band may be positioned on the listener's head 20 with the pads 24 transversely in contact with the listener's head behind the ears 18 whereby sounds can be transmitted from the earphones 26 into the ears 18. The ear extenders 30 are removably secured to the pads 24 so that when the earphones 26 are deactivated sounds can be amplifyed and transmitted into the ears 18 by the ear extenders 30.

FIG. 6 also shows one adjustable flared member 32 mounted to curved edge 34 of the cup shaped ear extender 30 so that the flared member 32 can properly direct the amplified sounds into the ear 18. A multiple of flared members 32 can also be mounted onto the curved edge 34 of the ear extenders 30 to increase the amplification of sounds into the ear 18 if so desired.

FIG. 7 shows a head band 36 that is telescopic so as to be adjustable to fit about various size heads 20. Part 38 snugly slides into slot 40 in part 42 for the adjustment thereof.

While certain novel features of this invention have been shown and described and are pointed out in the annexed claims, it will be understood that various omissions, substitutions and changes in the forms and details of the device illustrated and in its operation can be made by those skilled in the art without departing from the spirit of the invention.

What is claimed is:

1. An acoustic device for amplifying sounds which comprises:
   (a) a pair of ear extenders, each said ear extender being larger than a normal adult human ear and constructed out of lightweight sound reflective material; and
   (b) a head band adapted to fit closely about a listener's head with ends engaging the head behind the ears, said ear extenders being secured to said ends so that said head band may be positioned on said listener's head with said ear extenders extending transversely outward of said head, further comprising a pair of relatively soft pads, each said pad mounted to each of said ear extenders adjacent said ends so as to make contact with said listeners head behind said ear for a comfortable fit thereon.

2. An acoustic device as recited in claim 1, wherein said head band is telescopic so as to adjustable to fit about various size heads.

3. An acoustic device as recited in claim 1, wherein each said ear extender is flat shaped.

4. An acoustic device as recited in claim 3, wherein each said flat shaped ear extender is bent along one side.

5. An acoustic device for amplifying sounds which comprises:
   (a) a pair of relatively soft pads;
   (b) a pair of earphones, each said earphones mounted within one of said pads;
   (c) a head band adapted to fit about a listener's head, said pads being secured to said head band so that said head band may be positioned on said listener's head with said pads transversely in contact with said listener's head behind said ears and extending transversely outward whereby sounds can be transmitted from said earphones into said ears; and
   (d) a pair of snap on cup shaped ear extenders, each said ear extenders removeably secured to said pads to extend transversely outward of said pads so that when said earphones are deactivated sounds can be amplified and transmitted into said ears by said ear extenders.

6. An acoustic device as recited in claim 5, further comprising at least one adjustable flared member mounted on a curved edge of each said cup shaped ear extender so that said flared members can properly direct further amplified sounds into said ear.

* * * * *